United States Patent [19]
Glatt

[11] Patent Number: 5,795,152
[45] Date of Patent: Aug. 18, 1998

[54] ACCESSORY DEVICE FOR A DENTAL ARTICULATOR AND METHOD FOR USE IN FABRICATING DENTAL PROSTHETICS

[76] Inventor: Marc J. Glatt, 4325 Regalwood Ter., Burtonsville, Md. 20866

[21] Appl. No.: 828,361

[22] Filed: Mar. 28, 1997

[51] Int. Cl.[6] ............................................. A61C 11/00
[52] U.S. Cl. ........................................ 433/60; 433/54
[58] Field of Search ............................ 433/54, 55, 56, 433/60, 63, 65

[56] References Cited

U.S. PATENT DOCUMENTS

| | | | |
|---|---|---|---|
| 2,037,003 | 4/1936 | Boatner | 433/63 |
| 2,608,762 | 9/1952 | Fox | 433/63 X |
| 2,621,406 | 12/1952 | McPhee | 433/63 X |
| 2,716,815 | 9/1955 | Ford | 433/63 X |
| 4,182,039 | 1/1980 | Preti | 433/54 |
| 4,278,426 | 7/1981 | Schwartz | 433/56 |
| 4,459,108 | 7/1984 | Mack | 433/55 |
| 4,573,915 | 3/1986 | Merz | 433/54 |
| 4,609,351 | 9/1986 | Blair | 433/55 |
| 4,624,639 | 11/1986 | Wong | 433/56 |
| 4,634,377 | 1/1987 | Behrend | 433/73 |
| 4,639,220 | 1/1987 | Nara | 433/69 |
| 4,659,311 | 4/1987 | Raskin | 433/55 |
| 4,886,453 | 12/1989 | Ludwigs | 433/54 |
| 5,190,455 | 3/1993 | Schreiber | 433/54 |

OTHER PUBLICATIONS

"Suggested Procedures for the Arrangement and Articulation of Trubyte Anterior and Posterior Teeth", Dentsply Inter. Inc., York, PA, Aug. 1993.

*Primary Examiner*—Nicholas D. Lucchesi
*Attorney, Agent, or Firm*—Charles Blake Sajonic

[57] ABSTRACT

The present invention relates generally to an accessory device for a dental articulator and method for using the device in the construction of dental prosthetics. More particularly, the present invention relates to a vertically adjustable occlusal plane table and mounting platform that may be used with a variety of articulators in the mounting of casts, the selection of an occlusal plane, the positioning and setting of upper and lower artificial teeth, and other procedures in the fabrication of removable and fixed dental restorations.

9 Claims, 5 Drawing Sheets

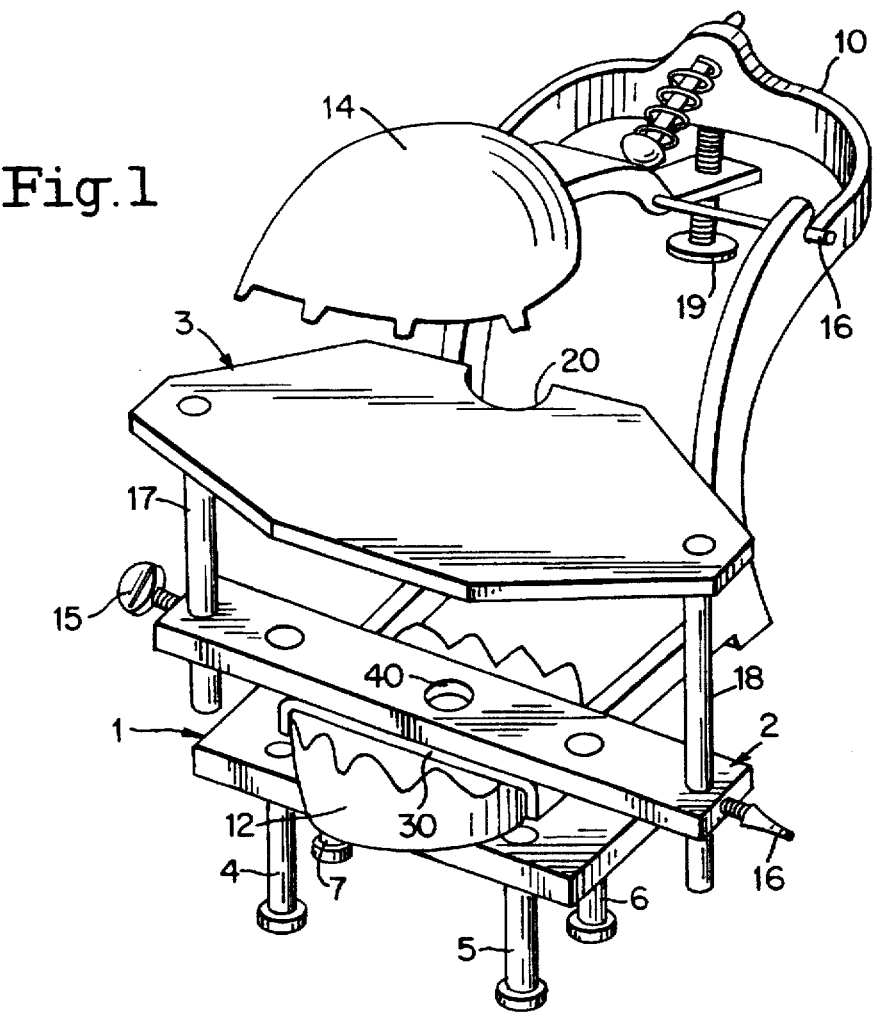
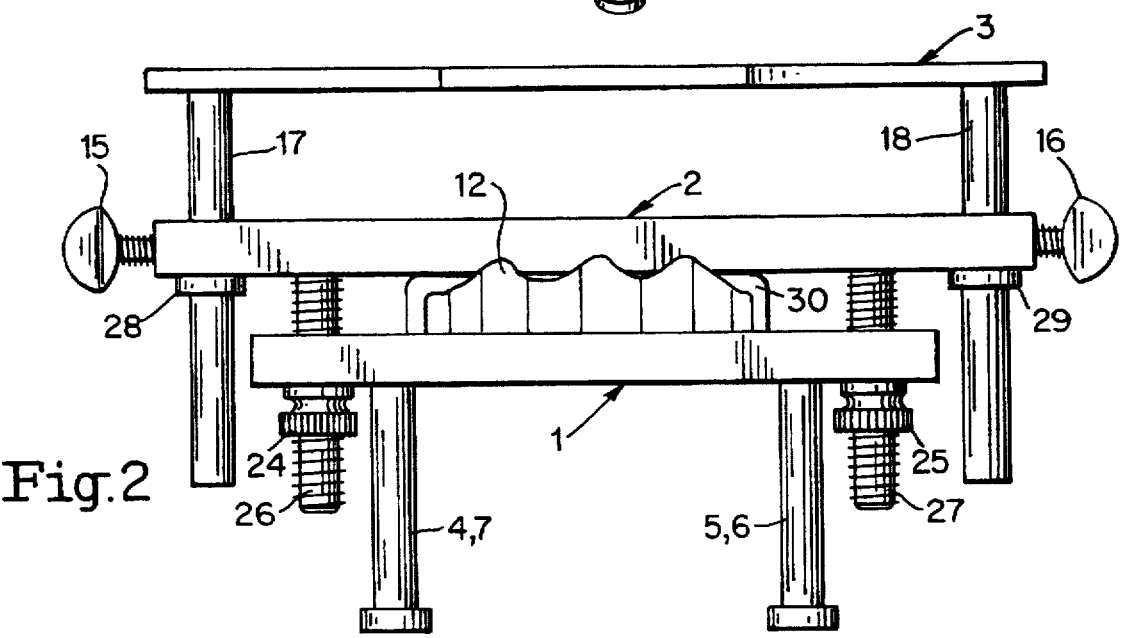

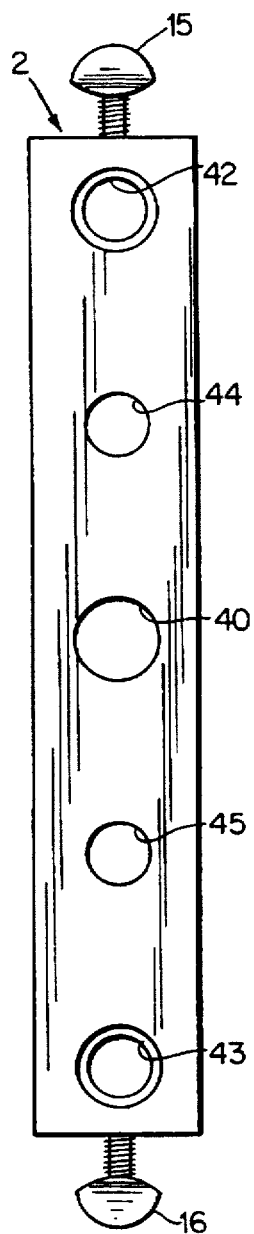
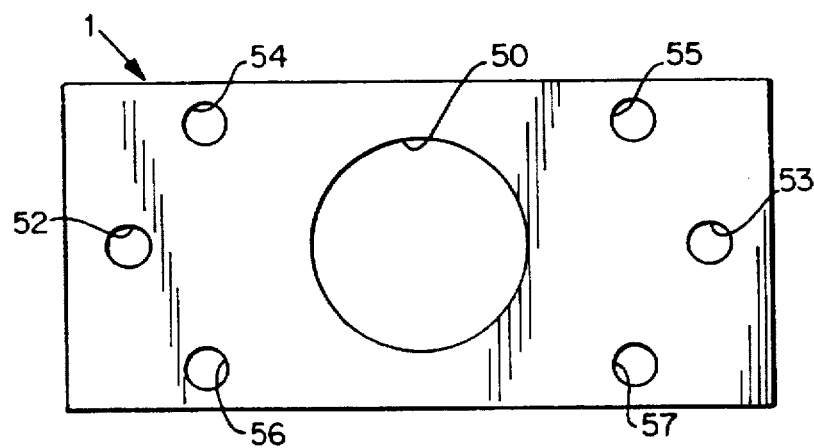
Fig.7
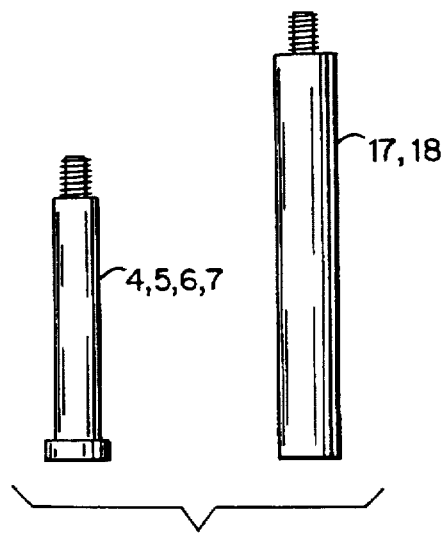
Fig.6
Fig.8

ACCESSORY DEVICE FOR A DENTAL ARTICULATOR AND METHOD FOR USE IN FABRICATING DENTAL PROSTHETICS

This application claim priority under USC 119 (A) of provisional application Ser. No. 60/014,738, Mar. 30, 1996.

BRIEF DESCRIPTION OF THE INVENTION

The present invention relates generally to an accessory device for a dental articulator and method for using the device in the construction of dental prosthetics. More particularly, the present invention relates to a vertically adjustable occlusal plane table and mounting platform that may be used with a variety of articulators in the mounting of casts, the selection of an occlusal plane, the positioning and setting of upper and lower artificial teeth, and other procedures in the fabrication of removable and fixed dental restorations.

BACKGROUND OF THE INVENTION

One of the principal difficulties involved in the construction of dental prosthetics is the positioning and placement of artificial teeth. Although many devices are available to assist in this procedure, it remains an art that is performed largely by hand with the aid of relatively simple tools. Devices, such as the one described in U.S. Pat. No. 4,639,220 issued to Nara et al., are available for use with specific articulators to take accurate and detailed measurements of the patient, including the occlusal plane, and to transfer those measurements to an articulator. These devices, however, are not commonly used in everyday practice because of their complexity, cost, and requirement for longer patient examinations. Instead, current industry practice favors the simple hinge-type articulator. Jaw movement is simulated using rotation along one axis. An occlusal plane is established using a simple hand-held plate for aligning and placement of the artificial teeth, and the artificial teeth are placed in accordance with published guidelines such as those provided in, "*Suggested Procedures for the Arrangement and Articulation of Trubyte Anterior and Posterior Teeth,*" Dentsply International Inc., York, Pa., Form No. 4087-A (90045) 8/93, which is incorporated herein by reference. Although not as accurate as the procedures that use Nara or other types of articulators, this provides a simple and relatively inexpensive means of dental fabrication.

Some articulators include mounting platform attachments that are fastened to the articulator such that a flat or slightly curved surface is provided between the upper and lower parts of the articulator. These attachments can be used to mount the upper cast or model and to position or set the upper artificial teeth. Although it offers an improvement in accuracy over the previously discussed hand held plate, the platform is designed for use with a specific articulator model and is not generally fit for use with other models or types of articulators. Moreover, the platform is fixed at a predetermined height. With the variation in patient requirements and the alteration of bite blocks in the bite registration process, the use of the fixed position platform is less than optimal.

U.S. Pat. No. 4,624,639, issued to Brian W. Wong provides an adjustable occlusal plane table and method of use for orthognathic set-ups. This invention, however, is intended for use in cases involving the surgical adjustment of the maxillary and/or mandible to correct an existing malocclusion. Although it could be used to perform some of the functions of the present invention, it has several limitations in such application. First it is designed for use with a specific articulator. As such, it cannot be used on other articulators such as the simple hinge-type articulator. Second, because of the shaft and sleeve length which are used to support the adjustable plane table, the Wong device appears to lack the clearance required to allow both casts and their fused bite records to be centered within the articulator for mounting purposes. Finally, the Wong device is not fixed in a level orientation relative to the lower member of the articulator and therefore must be adjusted with a leveling tool or other means each time the plane is moved.

As tooth placement is a critical part of the art of prosthetic dentistry, the present invention will help to prevent or mitigate several problems that can result from the improper placement of artificial teeth, such as premature wear, poor chewing ability, uneven occlusion, premature occlusion, premature resorption of residual ridges, uneven appearance, sore spots, and the perception of a poor fit.

OBJECTS AND SUMMARY OF THE INVENTION

Accordingly, one object of the present invention is to provide an accessory device for use with a variety of articulators in the construction of dental prosthetics.

Another object of the present invention is to enhance the features of a simple hinge-type articulator when used in combination with the present invention.

Another object of the present invention, is to provide a mounting platform for upper or lower models.

Another object of the present invention, is to provide a work surface with vertical adjustability between the upper and lower parts of an articulator that is fixable by the operator at a desired level.

A related object of the present invention is to provide a stable work surface for setting prosthetic teeth and performing other prosthetic construction procedures.

Another object of the present invention is to improve the accuracy, precision, and speed of dental prosthetic construction using standard articulators.

Another object of the present invention is to allow selection of a desired occlusal plane even when bite blocks are fused or otherwise altered.

Another object of the present invention is to provide a versatile tool that can be used for a number of procedures, including the construction of complete dentures, partial dentures, and crown and bridges.

The present invention relates to a vertically adjustable occlusal plane table and mounting platform that may be used with a variety of different types of articulators in the mounting of casts, the selection of an occlusal plane, the positioning and setting of upper and lower artificial teeth, and other procedures in the fabrication of removable and fixed dental restorations.

BRIEF DESCRIPTION OF THE DRAWINGS

FIG. 1 is a perspective view of an accessory device for a dental articulator in accordance with this invention.

FIG. 2 is a front view of the accessory device.

FIG. 6 is a bottom view of a middle plate.

FIG. 7 is a bottom view of a base plate.

FIG. 8 is a side view of a dowel and leg.

DETAILED DESCRIPTION OF THE INVENTION

Figure 3:
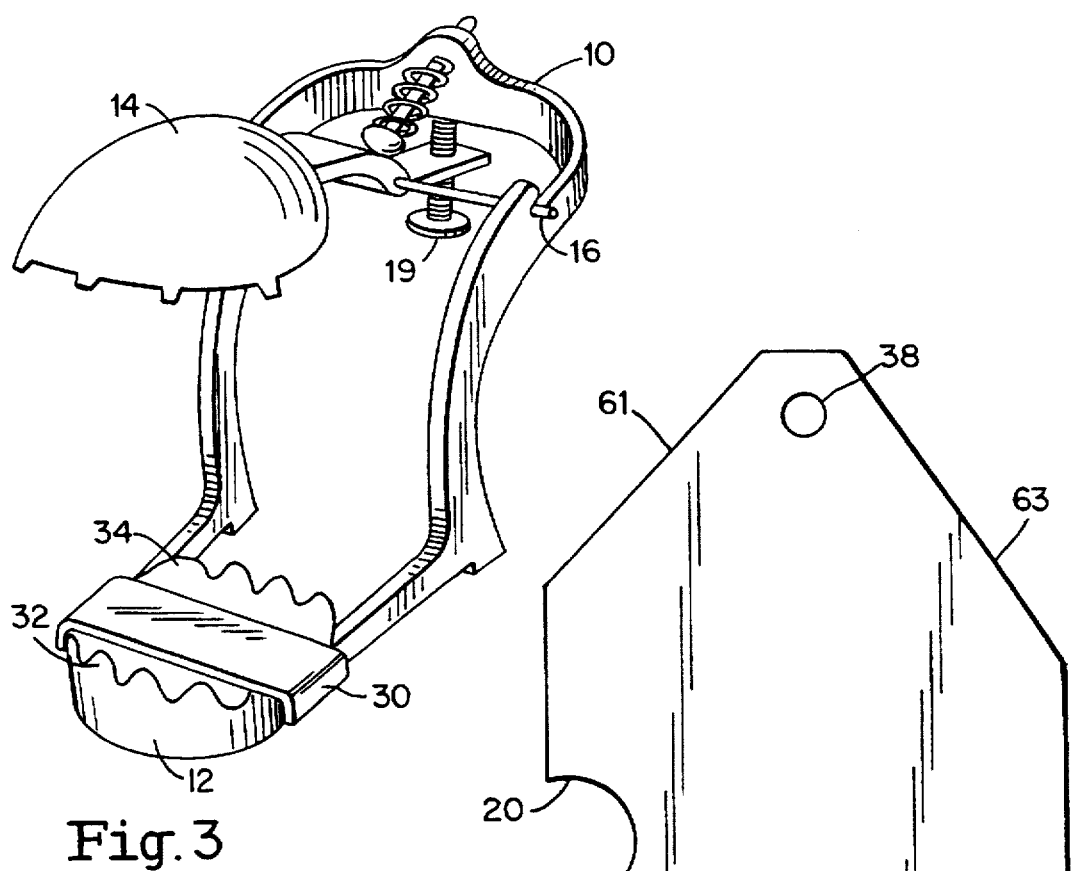
FIG. 3 is a perspective view of a dental articulator having a model mounting plate in accordance with this invention.

Referring to FIG. 1, an apparatus in accordance with the present invention is depicted. By way of overview, the apparatus can be viewed as including a number of major components that are used with a dental articulator, illustrated here by the simple hinge type articulator 10. Lower member 12 of the articulator is held stationary between base 1 and middle plate 2. Base 1, having legs 4–7, provides a stable platform to support both the device and articulator 10. Middle plate 2 has set screws 15–16, which when loosened, allow dowels 17–18 to slide freely. In this way, work surface 3 can be positioned at various elevations relative to top member 14 of the articulator. Throughout its range of motion, work surface 3 remains parallel to base 1 and middle plate 2, thus providing a repositionable reference plane. The size and shape of work surface 3 is such that it can be used as an occlusal reference plane and mounting platform, while avoiding any interference with the operation of articulator 10. For example, notch 20 provides the necessary clearance for adjustment knob 19 when top member 14 of the articulator is rotated upwards along axis 16 causing the adjustment knob to move down and towards work surface 3. In addition to its use as an occlusal reference plane and mounting platform, work surface 3 provides a convenient place to support tools, measuring devices, and the like during dental fabrication. If desired, work surface 3 also can be used to support a curved occlusal reference surface as opposed to a flat surface.

Referring to FIG. 2, a front view of the accessory device is illustrated. Lower member 12 of the articulator is held between base 1 and middle plate 2 using bolts 26–27 and knurled nuts 24–25. Set screws 15–16 and knurled nuts 24–25 are used for convenience so that no tools are needed to use the present invention. The device can be mounted to an articulator, and work surface 3 can be adjusted as necessary without the need for wrenches, screw drivers, or the like. PTFE bushings 28–29 in middle plate 2 allow dowels 17–18 to slide while providing a snug fit for lateral stability. Middle plate 2 is longer than both work surface 3 and base 1 to provide the necessary clearance for dowels 17–18 and bolts 26–27, and to provide thumb or finger rests when extending or retracting the dowels. Legs 4–7 are of sufficient length to prevent dowels 17–18 and bolts 26–27 from touching the support surface.

Turning to FIG. 3, model mounting piece 30 is provided for use with lower member 12 of the articulator. Without such a piece, the accessory device could not be mounted to the simple hinge type device as depicted here by articulator 10. On a simple hinge type articulator, the lower dental model is mounted directly to lower member 12 of the articulator typically using plaster. In the present invention, model mounting piece 30 is placed within the plaster setting along with the lower dental model. When the model is removed, the top surface of model mounting piece 30 is exposed, providing a flat and uniform contact surface for middle plate 2. As described below, ridges 32 and 34 are purposely made in the cast to ensure that the model, which has corresponding notches, is placed in the same position and orientation when it is returned to lower member 12. The width of piece 30 is slightly greater than the width of middle plate 2 to prevent interference from ridges 32 and 34, even though it is desirable to have the ridges rise above the top of piece 30 as discussed in greater detail below.

Having provided a general overview of the major components, attention is turned to a general description of how the apparatus is used with an articulator. Although it can be mounted to either the upper or lower member of an articulator, it is generally attached to the latter, and therefore is described in this orientation. Knurled nuts 24–25 are loosened or removed altogether from bolts 26–27 to allow base 1 to be separated from middle plate 2. The device is then placed on an articulator such that the top surface of base 1 is in contact with the bottom surface of the lower member 12 of the articulator, and the bottom surface of middle plate 2 is in contact with the top surface of said lower member. Knurled nuts 24–25 are then tightened to secure the device to the articulator. The device is thus clamped to the articulator by base 1 and middle plate 2.

Having fixed base 1 and plate 2 relative to the lower member 12 of the articulator and to each other, set screws 15–16 are then loosened to allow dowels 17–18 to slide freely through middle plate 2. In this way, the position of work surface 3 can be adjusted to the desired position above the lower member of the articulator while maintaining a substantially level orientation parallel to the bottom members. When work surface 3 is at the desired position, set screws 15–16 are tightened to lock dowels 17–18 in position. This provides the operator with a stable work surface at the desired position within an articulator. The shape and size of the present device is such that it provides a convenient work surface that fits within various articulators without interfering with other articulator functions. This work surface can be used for the mounting of casts, the selection of an occlusal plane, the positioning and setting of upper and lower artificial teeth, and other procedures in the fabrication of removable and fixed dental restorations.

Having provided a general overview of the present invention, attention is turned to a more detailed description of the various physical components of the preferred embodiment.

Figure 4:
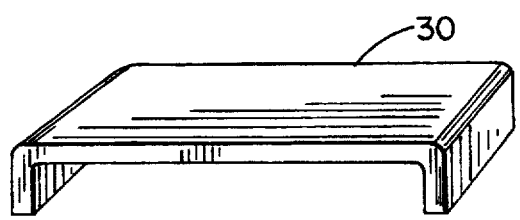
FIG. 4 is a perspective view of a model mounting plate.

Turning to FIG. 4, model mounting piece 30 is illustrated in perspective. In the preferred embodiment, piece 30 is made from a single piece of ⅛ inch aluminum that is bent along opposite edges to form two support legs. The top surface of piece 30 is approximately 3 inches in length and 1-5/16 inches in width. When resting on its support legs, piece 30 is approximately ⅝ inches in height.

Figure 5:
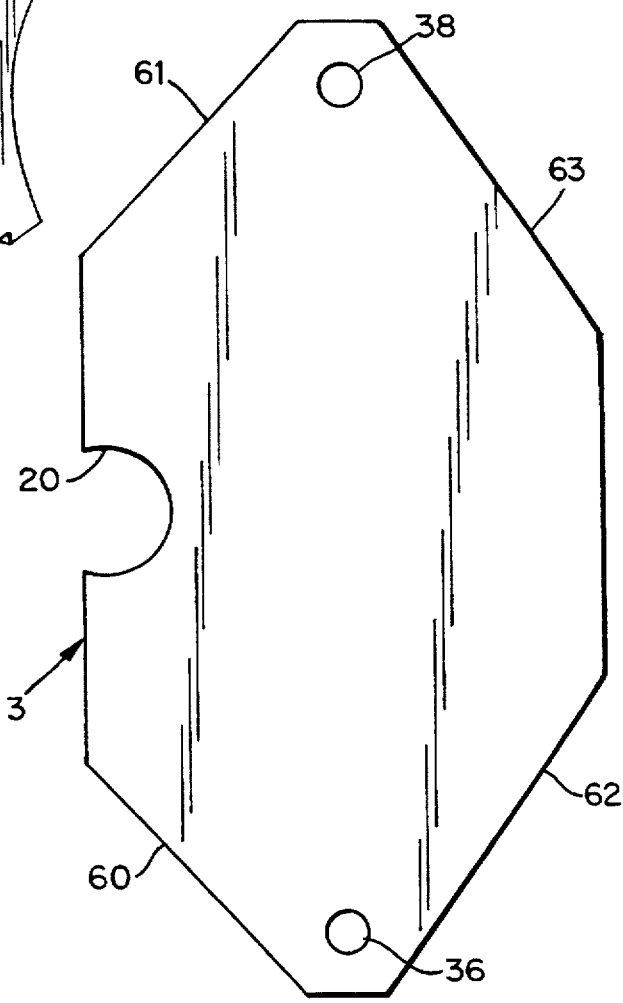
FIG. 5 is a top view of a work surface.

Turning to FIG. 5, the top of work surface 3 is illustrated. As described above, the size and shape of work surface 3 provides adequate work space while avoiding interference with articulator function. For example, notch 20 provides clearance for when the top member of the articulator is rotated. The back cutouts 61–62 allow clearance room for the support arms that are found on some of the larger articulators, while the front cutouts 63–64 allow more access, both visual and physical, to the work piece. In the preferred embodiment, top surface 3 is fabricated from ⅛ inch aluminum plate with an approximate length of 6 inches and a width of 3 inches. Holes 36 and 38 are drilled for attaching dowels 17–18. In the preferred embodiment, a 19/32 inch hole is used for this purpose.

Turning to FIG. 6, the bottom of middle plate 2 is illustrated. Middle plate 2 contains holes 44–45 for receiving bolts 26–27 and holes 42–43 for receiving dowels 17–18. Holes 42–43 contain PTFE bushings to allow dowels 17–18 to slide through the holes while maintaining a tight fit for lateral stability. The slip fit provided between the bushing and dowels 17–18, along with the fixation of the dowels in work surface 3, allows the work surface to travel away and toward middle plate 2 while staying parallel to the middle plate with little or no wobble or play. Any lateral instability, such as wobble or play in the position and orientation of work surface 3, is undesirable as it would result in an uneven or inconsistent reference plane. Thumb screws 15–16 are provided to fix the position of dowels 17–18 relative to middle plate 2, thus locking work surface 3 in the desired position.

A 7/16 inch diameter hole, 40, is provided at the center of middle plate 2 because on some articulators the lower and upper members have a mounting plate that is secured to the articulator with a screw in the center of the member. Typically, there are one or two small projections on the articulator member, which have corresponding recesses in the mounting plate, the purpose of which is to center the mounting plate when it is attached to the articulator. This configuration of screw and centering pins requires clearance in order to allow the underside of middle plate 2 to contact a flat surface. Hole 40 is thus provided at the center of middle plate 2 to receive the screw, and the width of plate 2 is such that the centering pins on most articulators, such as those sold under the trademarks HANAU, DENAR, and SHOFU, fall outside the width of middle plate 2, thus avoiding any interference with articulator function. In this way middle plate 2 can lay flat against the top side of the lower or upper member of the articulator.

Referring to FIG. 7, base 1 is constructed of rigid material such as 3/8 inch aluminum plate to provide a flat, smooth, and substantially rigid surface. It contains holes 52–53 for receiving bolts 26–27. Hole 50 is provided in the center of plate 1 to provide a stable contact surface when the present invention is used with certain articulators. As some articulators have a bolt head or some other raised surface near the center of the lower half of the articulator, hole 50 allows the bottom of plate 1 to receive this bolt head or otherwise raised surface such that plate 1 rests evenly on the flat portion of the articulator's underside. Base 1 is equipped with four legs (shown in FIG. 1 and 2), which are fastened to the bottom of the plate near each corner using holes 54–57. The legs are each 1/4–20 male threaded dowel shoulder bolts as illustrated in FIG. 8. When fastened to plate 1, they extend 1 11/16 inches from the bottom of the plate, providing clearance between base 1 and any object supporting the legs. This ensures that dowels 17–18 do not contact the support surface when attached to an articulator even in the fully contracted position. In the preferred embodiment, hole 50 is 1 5/16 inches in diameter and holes 52–53 are 1/4–20 female threaded to approximately half of the thickness of base 1. The overall dimension of base 1 is approximately 4½ by 2 inches.

Turning to FIG. 8, dowels 17–18 are 2⅛ inch stainless steel shoulder bolts with a of 1/4-inch by 10/32-inch male threaded top. Legs 4–7 are 2-inch stainless steel should bolts with a 1/4-inch by 10/32-inch thread. Legs 4–7 have an enlarged diameter at their base of stability when supporting the device.

As described above, the shape and dimension of base 1, middle plate 2, and work surface 3, result in a highly versatile tool for use with a variety of articulators. For example, dowels 17–18 and bolts 26–27 are located outside the work area, at the side and bottom of the present device. This allows a full range of vertical adjustment without interfering in the work space. At one extreme, work surface 3 can be brought into contact with middle plate 2, with middle plate 2 in contact with lower member 12, effectively collapsing the device to provide maximum clearance between lower and upper members of an articulator.

Figure 9:
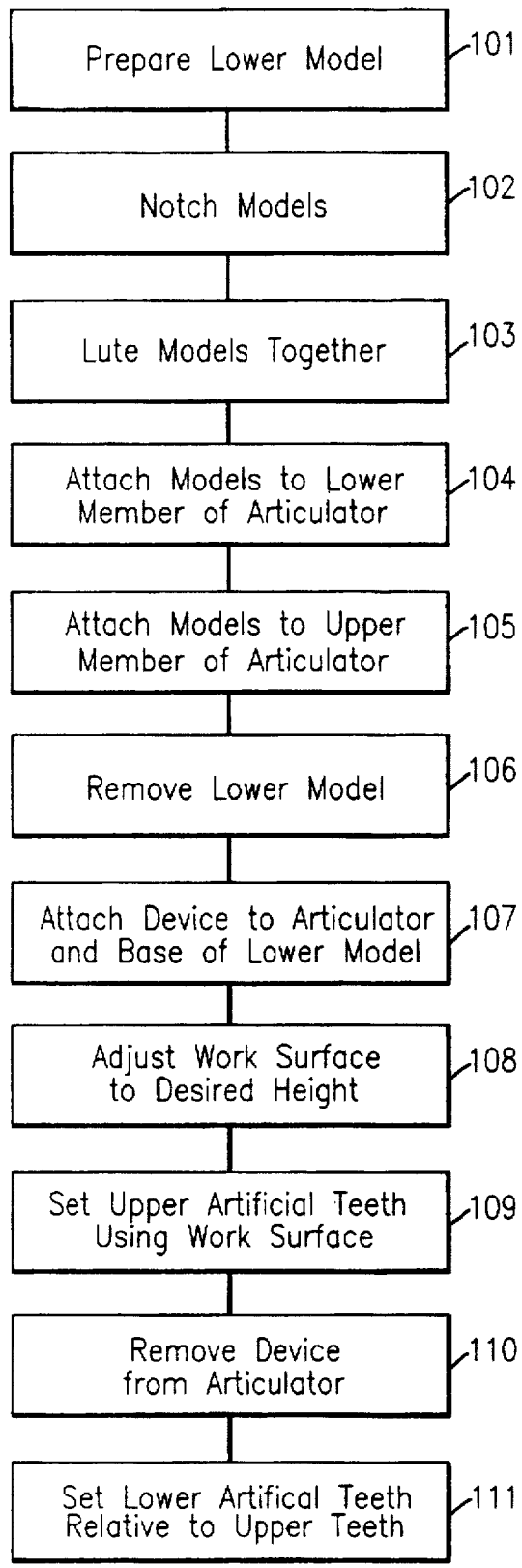
FIG. 9 is a flowchart illustrating the process for using the present device with simple hinge type articulators.

Having provided an overview of suitable hardware elements to be used in accordance with the present invention, attention presently turns to its method of use. Turning to FIG. 9, a stepwise method for using the device in the fabrication of dental prosthetics is illustrated. By way of example, this procedure is applied when using the present device in combination with, and attached to, the lower member of a simple hinge type articulator. With minor modifications, however, this procedure can be used with other types of articulators and with the device attached to either the lower or upper member of the articulator.

The first step, 101, in using the present device for the fabrication of dental prosthetics is to prepare the bottom surface of the lower model. When resting on a horizontal surface, such as a table top, the ridges of the model should appear in the same position and orientation as they would appear in the mouth with the patient's head in an erect position. In general, the ridges are balanced from front to back and side to side in a relatively level or even fashion. This can be accomplished by either initially forming the model on a flat surface such as a plane of glass or plexiglass, or by using a model trimmer to level the bottom surface after the model has set. In either case, the ridges of the lower model should appear in the same orientation as they would appear in the patient's mouth when sitting or standing upright.

The next step, 102, is to notch the upper and lower models for subsequent reference. The notches on the lower model should be outside of the contact area of middle plate 2 and model mounting piece 30 so as not to interfere when the present device is attached to an articulator. This is performed by outlining the dimension of model mounting piece 30 across the bottom of the lower model using a pencil or other means. Notches can then be made outside these lines without interfering in the subsequent process steps. The next step, 103, is to lute the upper and lower models together in their proper bite relationship. This step is performed in accordance with standard practice.

In step 104, the luted models are attached to the lower member of the articulator. This is performed by first luting the model mounting piece 30 to the bottom of the lower model. Separator material is then applied to the exposed areas of the underside of the lower model, then a gypsum patty is formed on the lower member of the articulator with the articulator supported on a flat surface. Model mounting piece 30, which is attached to the lower model, is then placed in the patty such that legs of the model mounting piece straddle the lower member and sit flat on the supporting surface. The next step, 105, is to attach the upper model to the articulator while it is still luted to the lower model in the proper bite relationship. This is accomplished in accordance with normal practice. In step 106, the lower model is removed, leaving the upper model attached to the upper member of the articulator, and the lower mounting, including mounting piece 30, attached to the lower member of the articulator.

The device can now be mounted to the lower member of the articulator. This is accomplished in step 107 by first loosening or removing nuts 26–27 to allow middle plate 2 to move away from base 1. The bottom member of the articulator with the incorporated model mounting piece 30 is then placed between base 1 and middle plate 2 such that notch 20 is facing the hinge of the articulator and middle plate 1 is bearing on the top surface of mounting piece 30. Nuts 26–27 are then tightened to secure the device to the articulator. In step 108, work surface 3 is positioned to the desired height between the upper and lower members of the articulator. This is done by loosening set screws 15–16 and sliding work surface 3 to or from middle plate 2. The upper artificial teeth can then be set in step 109 using work surface 3 as a reference and support platform. In step 110, the device is remove from the articulator by loosening or removing nuts 24–25, moving middle plate 2 away from base 1, and removing the lower member of the articulator from between base 1 and middle plate 2, thus exposing the top surface of mounting piece 30 and the ridges formed in step 104. The lower artificial teeth can then be set in step 111 using the previously set upper teeth for reference. This is accomplished by first reattaching the lower model to its lower portion and then using standard procedures.

Figure 10:
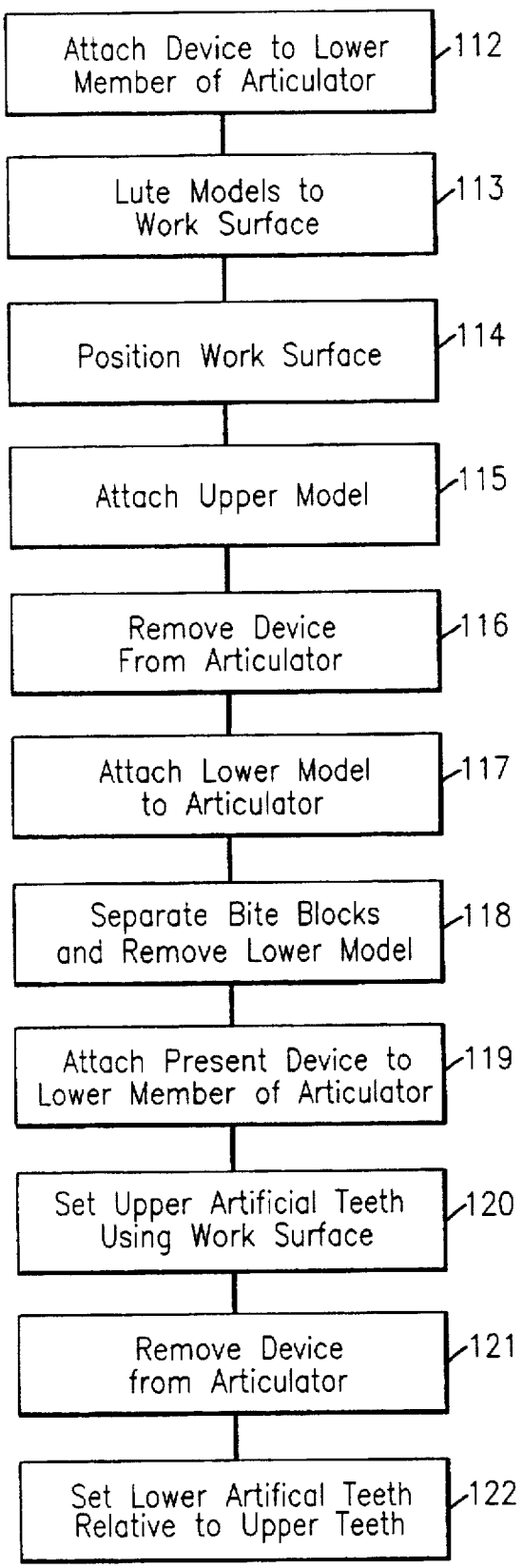
FIG. 10 is a flowchart illustrating the process for using the present device with other types of articulators.

Turning to FIG. 10, a stepwise method for using the present device with other types of articulators is illustrated. The device is first attached to the lower member of the articulator in step 112 by placing base 1 under the lower member of the articulator and sliding bolts 26–27 through holes 52–53 such that middle plate 2 is in contact with the top portion of the lower member of the articulator. The device is secured to the articulator by tightening nuts 24–25. The models are luted together and to work surface 3 in step 113, and the position of the work surface is adjusted to a position in step 114 such that the desired occlusal plane is centered vertically between the upper and lower members of the articulator. In step 115, the upper model is attached to the upper member of the articulator with gypsum or similar means. The device is then removed from the articulator in step 116 leaving the upper and lower models suspended from the upper member of the articulator. In step 117, the lower model is attached to the bottom member of the articulator. In step 118, the bite blocks are separated and the lower model is removed from the articulator. The present device can then be reconnected to the lower member of the articulator in step 119. The upper and lower artificial teeth can be set in steps 120 to 122 using the same procedures as described above for use with the simple hinge type articulators.

From the description above, a number of advantages of the present invention become evident. First, the device provides a versatile accessory device for use with a variety of articulators in a number of procedures, including the construction of complete dentures, partial dentures, and crown and bridges. It renders the simple hinge type articulator a better device when used in combination with the present invention by providing vertical adjustability between the upper and lower parts of an articulator that is fixable by the operator at a desired level without interfering with other articulator functions. The present invention also provides a mounting platform for upper or lower models and a stable work surface for setting prosthetic teeth and performing other dental construction procedures. When using the device, the proper occlusal plane can be established even when bite blocks are fused or otherwise altered. In general, the present invention improves the accuracy, repeatability of results, and speed of dental prosthetic construction using industry standard articulators.

The foregoing description of specific embodiments of the present invention have been presented for purposes of illustration and description. They are not intended to be exhaustive or to limit the invention to the precise forms disclosed, and obviously many modifications and variations are possible in light of the above teaching. For example, work surface 19 can be shaped as a curved surface. Various shapes, dimensions, materials, and fasteners can be used other than the ones described above to perform the same function. The embodiments illustrated and described above were chosen to best explain the principles of the invention and its practical application, thereby enabling others skilled in the art to best utilize the invention and various embodiments with various modifications as are suited to the particular use contemplated. It is intended that the scope of the invention be defined by the following Claims and their equivalents.

We claim:

1. An accessory device for use with various types of dental articulators including a simple hinge type articulator, said accessory device comprising: a base; a middle plate attached to said base; a work surface, substantially parallel and adjustably attached to said middle plate; and means for attaching said device to various types of dental articulators wherein said means includes a model mounting piece for providing a substantially flat surface upon which said middle plate is secured when using the accessory device with a simple hinge type articulator.

2. An accessory device as recited in claim 1, wherein said work surface includes a notch and cutouts to prevent interference with normal articulator function.

3. An accessory device as recited in claim 2, wherein said base includes one or more holes for receiving a bolt.

4. An accessory device as recited in claim 3, wherein said means for attaching said device to various types of dental articulators, said articulators having upper and lower members, includes a plurality of bolts and nuts, said bolts having one end threaded into said middle plate and the other end free for passing through said one or more holes in the base and receiving said nuts for securing said base and middle plates to one of the members of the articulator.

5. An accessory device as recited in claim 4, wherein said middle plate includes one or more holes for receiving a dowel.

6. An accessory device as recited in claim 4, further comprising one or more dowels and set screws, said one or more dowels having one end attached to said work surface and the other end slidably disposed within said one or more dowel receiving holes.

7. An accessory device as recited in claim 6 wherein said middle plate includes a central hole.

8. An accessory device as recited in claim 7, wherein said base includes a central hole and a plurality of legs.

9. A method of fabricating dental prosthetics, including the steps of attaching a model mounting piece to one member of an articulator; attaching an accessory device having a work surface to the articulator member having the mounting piece attached thereto using the flat surface provided by said model mounting piece attaching step;

adjusting the elevation of the work surface to the desired occlusal plane position;

setting a first set of artificial teeth using said work surface as a reference plane;

removing the accessory device from the articulator; and setting a second set of artificial teeth in relation to said first set of artificial teeth.

* * * * *